United States Patent
Hu et al.

(10) Patent No.: US 10,898,883 B2
(45) Date of Patent: Jan. 26, 2021

(54) SILICALITE-1 MOLECULAR SIEVE-BASED CATALYST AND PREPARATION METHOD FOR 1,2-PENTANEDIOL USING SAID CATALYST

(71) Applicant: WANHUA CHEMICAL GROUP CO., LTD., Shandong (CN)

(72) Inventors: Jianglin Hu, Shandong (CN); Yunhai Liu, Shandong (CN); Xinjian Bian, Shandong (CN); Yuan Li, Shandong (CN); Qingmei Jiang, Shandong (CN); Changsheng Chen, Shandong (CN); Yanfang Song, Shandong (CN); Yang Yang, Shandong (CN); Wei Zeng, Shandong (CN); Ke Ding, Shandong (CN); Hengdong Yang, Shandong (CN); Kun Wang, Shandong (CN); Weiqi Hua, Shandong (CN)

(73) Assignee: Wanhua Chemical Group Co., Ltd., Shandong (CN)

( * ) Notice: Subject to any disclaimer, the term of this patent is extended or adjusted under 35 U.S.C. 154(b) by 0 days.

(21) Appl. No.: 16/622,480

(22) PCT Filed: Aug. 2, 2017

(86) PCT No.: PCT/CN2017/095643
§ 371 (c)(1),
(2) Date: Dec. 13, 2019

(87) PCT Pub. No.: WO2019/014969
PCT Pub. Date: Jan. 24, 2019

(65) Prior Publication Data
US 2020/0139353 A1  May 7, 2020

(30) Foreign Application Priority Data
Jul. 20, 2017   (CN) .......................... 2017 1 0595213

(51) Int. Cl.
*B01J 29/035* (2006.01)
*B01J 35/00* (2006.01)
(Continued)

(52) U.S. Cl.
CPC ........... *B01J 29/0354* (2013.01); *B01J 23/42* (2013.01); *B01J 23/52* (2013.01); *B01J 35/0013* (2013.01);
(Continued)

(58) Field of Classification Search
CPC .. B01J 29/0354; B01J 35/0013; B01J 35/023; C07C 29/141; C07C 2523/42; C07C 2523/52; C07C 2529/035
See application file for complete search history.

(56) References Cited

U.S. PATENT DOCUMENTS 4,479,021 A   10/1984   Issler et al.
4,605,795 A   8/1986   Siegmeier et al.
(Continued)

FOREIGN PATENT DOCUMENTS

CN   1552684 A    12/2004
CN   101857524 A  10/2010
(Continued)

OTHER PUBLICATIONS

C107442155, Liu, H. et al., Preparation method and catalytic application of silicalite-1 singel crysal-coated nanopalladium-loaded core shell, English translation, 7 pages (Year: 2017).*
(Continued)

*Primary Examiner* — Yate' K Cutliff
(74) *Attorney, Agent, or Firm* — Michael Best and Friedrich LLP (57) ABSTRACT

An organic-base functionalized silicalite-1 molecular sieve-encapsulated metal nanoparticles catalyst and a preparation method therefor, as well as a method for preparing 1,2-pentanediol from biomass-derived furfuryl alcohol by hydrogenolysis using said catalyst. When the catalyst is used in a reaction preparing 1,2-pentanediol from furfuryl alcohol by hydrogenolysis, the catalyst has high hydrogenolysis
(Continued)

activity under relatively mild reaction conditions, significantly increasing the conversion rate of furfuryl alcohol and 1,2-pentanediol selectivity in the reaction, while also not generating obvious byproducts furfuryl alcohol polymers; the catalyst has good stability and long life, and may be recovered for reuse after the reaction is complete by means of a simple filtration, greatly reducing reaction costs and separation difficulty.

21 Claims, 3 Drawing Sheets

(51) Int. Cl.
    *C07C 31/20*     (2006.01)
    *B01J 23/42*     (2006.01)
    *B01J 23/52*     (2006.01)
    *B01J 35/02*     (2006.01)
    *C07C 29/141*     (2006.01)

(52) U.S. Cl.
    CPC ........... *B01J 35/023* (2013.01); *C07C 29/141* (2013.01); *C07C 31/20* (2013.01); *C07C 2523/42* (2013.01); *C07C 2523/44* (2013.01); *C07C 2523/52* (2013.01); *C07C 2529/035* (2013.01)

(56) References Cited

U.S. PATENT DOCUMENTS

| | | | |
|---|---|---|---|
| 2008/0064905 A1 | 3/2008 | Krimmer et al. | |
| 2016/0129429 A1* | 5/2016 | Kegnæs et al. | C07C 5/2737 585/467 |
| 2017/0036197 A1* | 2/2017 | Kegnæs | B01J 35/0006 |

FOREIGN PATENT DOCUMENTS

| | | | |
|---|---|---|---|
| CN | 102134180 A | 7/2011 | |
| CN | 102180769 A | 9/2011 | |
| CN | 102924243 A | 2/2013 | |
| CN | 104016831 A | 9/2014 | |
| CN | 104370702 A | 2/2015 | |
| CN | 106000449 A | 10/2016 | |
| CN | 106540662 A | 3/2017 | |
| CN | 107442155 A * | 12/2017 | ............. B01J 29/03 |
| JP | 2013044579 A | 3/2013 | |
| WO | 2012152849 A1 | 11/2012 | |
| WO | 2015174249 A1 | 11/2015 | |

OTHER PUBLICATIONS

International Search Report for corresponding International Application No. PCT/CN2017/095643 dated Apr. 26, 2018.
Bin Zhang et al., "Selective Conversion of Furfuryl Alcohol to 1,2-Pentanediol Over a Ru/Mnox Catalyst in Aqueous Phase", The Royal Society of Chemistry, Green Chemistry, vol. 14 pp. 3402-3409 (Dec. 2012).
Chinese First Office Action dated Nov. 22, 2019 for corresponding Chinese Application No. 201710595213.7.
Chinese Search Report dated Nov. 12, 2019 for corresponding Chinese Application No. 2017105952137.
Wenjie Xu et al., "Direct Catalytic Conversion of Furfural to 1,5-Pentanediol by Hydrogenolysis of the Furan Ring Under Mild Conditions Over Pt/Co2AlO4 Catalyst", The Royal Society of Chemistry, Chem. Commun., vol. 47, pp. 3924-3926 (2011).

* cited by examiner

SILICALITE-1 MOLECULAR SIEVE-BASED CATALYST AND PREPARATION METHOD FOR 1,2-PENTANEDIOL USING SAID CATALYST

TECHNICAL FIELD

The present invention relates to a catalyst, and specifically, relates to a catalyst based on a silicalite-1 molecular sieve. The present invention also relates to a method for preparing 1,2-pentanediol using the catalyst from furfuryl alcohol as a raw material.

BACKGROUND OF ART 1,2-pentanediol is a special dihydric primary alcohol and is widely used in many fields. For example, it is mainly used for the synthesis of a pesticide of propiconazole (a bactericide with high efficiency, low toxicity and broad-spectrum activity). In addition, 1,2-pentanediol has obvious polarity and non-polarity, and has excellent moisturizing effect in cosmetics or personal care products. In particular, 1,2-pentanediol also has antibacterial and antiseptic effects, therefore, it can be used to prepare products without antiseptics.

In conventional preparation methods, 1,2-pentanediol is obtained by epoxidation and then hydration using n-pentene as a raw material, as reported in patent documents U.S. Pat. Nos. 4,605,795, 4,479,021 and CN1552684, respectively. Propionic acid or formic acid, hydrogen peroxide, and the like are used in the preparation procedures thereof. Wherein n-pentene is mainly derived from the C5 fraction in the petrochemical industry. There are problems such as limited source of raw materials and high cost, potential safety hazards of peroxide oxidants used, and large amounts of base-neutralized wastewater, which greatly restrict the development of 1,2-pentanediol.

On this basis, various methods for preparing 1,2-pentanediol have been developed. For example, in patent document US20080064905, n-butyraldehyde is used to react with hydrocyanic acid and to form a corresponding cyanohydrin, and then 1,2-pentanediol is prepared by hydrolysis and hydrogenation. Patent document CN101857524 discloses that n-butanol and a thioether are first reacted under the catalysis of a strong acid to form a butyl sulfosalt, then the butyl sulfosalt is reacted with formaldehyde to form a corresponding epoxy pentane, and finally 1,2-pentanediol is prepared by hydrolysis. Patent document CN102180769 discloses that 1-hydroxy-2-pentanone is formed by the reaction of n-butyraldehyde and paraformaldehyde under the catalysis of a thiazole salt, then 1,2-pentanediol is formed by hydrogenation under the catalysis of Pd/C. In the above patent documents, the reaction costs thereof are reduced by replacing the C5 component with a relatively easily obtainable C4 component as a raw material source. However, the above methods have problems such as using highly toxic and polluting substances, complex catalytic systems and long process flows, and low product yield.

In recent years, more researches have been done on the process route of preparing 1,2-pentanediol by catalytic hydrogenolysis using inexpensive furfural and its derivative, furfuryl alcohol. The biomass derivative, furfural can be prepared from crop waste such as corn cob and bagasse, and is produced in large quantities in North China and Shandong province, with the advantages of wide range of sources and large reserves. Various chemicals synthesized from furfural and its derivative, furfuryl alcohol as the raw materials have attracted more and more attention because of their low cost and environmental protection.

Patent document CN102134180 and the literature (Chem. Commun., 2011, 47, 3924-3926) report a process for preparing 1,2-pentanediol by hydrogenation under mild conditions using furfural as a raw material and using a catalyst of noble metal Pt. However, the yield to 1,2-pentanediol of this process is only 16%.

Patent document CN102924243 discloses a method for preparing 1,2-pentanediol by one-step hydrogenation of furfural, in this method, a composite oxide containing CuO is used as a catalyst, 52.2% of 1,2-pentanediol selectivity is obtained under the reaction conditions of 180° C., 8 MPa and 20% methanol solution of furfural, the conversion rate of furfural is 92.0%, but the reaction conditions are harsh, and furfural is easily polymerized at a high temperature.

In the document Green Chem., 2012, 14, 3402, $Ru/MnO_x$ is used as a catalyst, 0.1M of KOH is added to adjust the system to be alkaline and to reduce the polymerization of furfuryl alcohol, a 1,2-pentanediol yield of 42.1% is obtained by selective hydrogenolysis of furfuryl alcohol under the condition of 150° C. and 3 MPa. However, the method has higher activity and selectivity only for the aqueous solution of furfuryl alcohol with low concentration (10 wt %), and reuse times for the catalyst is low.

In patent document WO2012152849, furfuryl alcohol is used as a raw material, and a hydrogenolysis is carried out at 230° C. under the action of a Pt catalyst to obtain an intermediate of 1-hydroxy-2-pentanone, and then a hydrogenation is carried out under the action of a Ru catalyst to obtain 1,2-pentanediol. The steps of this method are complicated and the reaction temperature thereof is high, and the polymerization of furfuryl alcohol is severe.

Patent document CN104016831 discloses a method for preparing 1,2-pentanediol by means of hydrogenation using furfuryl alcohol as a raw material. 35% of 1,2-pentanediol selectivity can be obtained by using $Ru/Al_2O_3$ as a catalyst and under the conditions of a weakly basic system (pH 7.6) adjusted by the addition of $Na_2CO_3$, 240° C., 10 MPa. The concentration of the aqueous solution of furfuryl alcohol is less than 10 wt %, and the efficiency is low.

Patent document WO2015174249 reports that a 1,2-pentanediol selectivity up to 47.6% can be obtained by a hydrogenation reaction at 170° C., 25 MPa, in the reaction, a Cu—Zn catalyst is used, pure furfuryl alcohol is used as raw material, and a small amount of NaOH (0.2% by weight of furfuryl alcohol) is added. The conversion of furfural is 89.2%, but the reaction conditions are extremely harsh.

Patent document CN104370702 discloses a method for preparing 1,2-pentanediol by liquid phase selective hydrogenolysis. A 1,2-pentanediol selectivity up to 41.4% can be obtained by a hydrogenation reaction using $Cu—B/SiO_2$ as a catalyst at conditions of 170° C., 8 MPa (pressure at room temperature) for 8 h. The conversion of furfural is 87.8%, but the polymerization of residual furfural cause the catalyst to be deactivated.

In summary, the catalysts in the prior art are quickly deactivated due to the easy polymerization (resinification) of furfural and furfuryl alcohol in a high temperature environment, and the product yields thereof are lowered. In addition, although the addition of the inorganic-base KOH or NaOH can reduce the polymeric side reactions, but it also inhibits the hydrogenolysis process, resulting in the 1,2-pentanediol selectivity not high enough, and too many by-products (such as tetrahydrofurfuryl alcohol), the subsequent separation is difficult and the base cannot be reused.

On the other hand, the MFI-type molecular sieve refers to a crystalline inorganic microporous compound having a structure type of MFI and a composition of pure silicon or silicon aluminum, wherein the molecular sieve having a composition of pure silicon is called as silicalite-1 (Si-MFI). The structure of MFI has two intersecting ten-membered-ring pore systems. One pore system is parallel to the crystallographic a-axis direction and has a sinusoidal shape with a pore size of about 0.53 nm×0.56 nm, the other pore system is parallel to the crystallographic b-axis direction, with a straight linear shape and a pore size of about 0.51 nm×0.55 nm. Silicalite-1 of pure silicon is usually prepared by hydrothermal method and has high thermal stability, and is widely used in the fields of separation, catalysts, etc. (Ind. Eng. Chem. Res., 2012, 51, 9492; Chem. Soc. Rev., 2015, 44, 7207).

SUMMARY

One of the objects of the present invention is to provide a catalyst which can be used in the reaction for preparing 1,2-pentanediol from furfuryl alcohol as a raw material. In a specific embodiment, the catalyst is capable of obtaining high hydrogenolysis activity and selectivity under mild conditions without producing obvious furfuryl alcohol polymer, and has good catalyst stability and long life.

A second object of the present invention is to provide a method for preparing 1,2-pentanediol using the catalyst from furfuryl alcohol as a raw material.

In order to achieve the above objects, the technical solutions of the present invention are as follows:

The present invention provides a catalyst based on silicalite-1 molecular sieve. Specifically, the present invention provides a catalyst for preparing 1,2-pentanediol by the hydrogenolysis of furfuryl alcohol, which comprises a carrier and an active component, wherein the carrier is a silicalite-1 molecular sieve surface-modified with an organic-base silane coupling agent, and the active component is metal nanoparticles encapsulated in the pores of the silicalite-1 molecular sieve.

Wherein the organic-base silane coupling agent is a compound represented by the following general formula (1):

(1)

Wherein, Base represents an organic basic group, such as an amino or a polyamine group, the amino is selected from a primary amino, a secondary amino and a tertiary amino; $R_1$, $R_2$ and $R_3$ represent $C_1$-$C_4$ alkyls, which are the same or different from each other; n is 1-10.

The organic-base silane coupling agent is preferably one or more of 3-aminopropyltriethoxysilane, 3-(2-aminoethylamino)propyltrimethoxysilane, diethylenetriaminopropyltrimethoxysilane and 3-(dimethylamino)propyltriethoxysilane. In the catalyst, the amount of the organic-base silane coupling agent is 0.01-5 mmol/g, preferably 0.1-2 mmol/g, based on the mass of the silicalite-1 molecular sieve without surface-modification (i.e., pure $SiO_2$).

The metal nanoparticles are nanoparticles of one or more of Ni, Co, Cu, Ru, Rh, Pd, Ir, Pt and Au; from the viewpoint of catalytic performance, the nanoparticles of Pt and/or Au are preferred. In the catalyst, the loading amount of the metal nanoparticles is 0.01-5 wt %, preferably 0.1-2 wt %, based on the mass of the silicalite-1 molecular sieve without surface-modification (i.e., pure $SiO_2$).

In another aspect, the present invention provides a method for preparing the catalyst, which comprises the following steps:

a) reducing an aqueous solution of soluble metal salt by using a reducing agent in the presence of a colloid stabilizing agent to obtain a colloid of metal nanoparticles;

b) adding an alcohol, ammonia water and a tetraalkyl orthosilicate to the colloid of metal nanoparticles obtained in step a), and distilling to remove water and alcohol after hydrolyzation, and then drying the residue to obtain a silica gel loaded with the metal nanoparticles;

c) crystallizing the silica gel loaded with the metal nanoparticles obtained in step b) by using hydrothermal method under the effect of a template agent, and calcinating at a high temperature to obtain a silicalite-1 molecular sieve encapsulated with metal nanoparticles;

d) modifying the surface of the silicalite-1 molecular sieve encapsulated with metal nanoparticles obtained in step c) by using an organic-base silane coupling agent in a solvent to obtain the catalyst.

Wherein in step a), the soluble metal salt is one or more of a metal nitrate, a metal acetate and a metal chloride, preferably one or more of nickel nitrate, cobalt acetate, copper nitrate, ruthenium chloride, palladium chloride, chloroiridic acid, chloroplatinic acid and chloroauric acid, more preferably chloroplatinic acid and/or chloroauric acid; the colloid stabilizing agent is selected from one or more of polyvinylpyrrolidone (PVP), polyethylene glycol, polyvinyl alcohol, Tween 20, Tween 80 and Span 20, preferably PVP; the reducing agent is selected from one or more of $NaBH_4$, formaldehyde and hydrazine hydrate, preferably $NaBH_4$.

In step a), the concentration of the aqueous solution of soluble metal salt is 0.1-2 mmol/L, and the ratio between the usage amounts of the colloid stabilizing agent, the soluble metal salt and the reducing agent is 5-20 g: 1 mmol: 5-15 mmol. The reducing conditions are preferably as follows: reacting in the air at −10-10° C. for 0.5-4 h.

In step b), the alcohol is a $C_1$-$C_4$ linear alcohol or a $C_3$-$C_4$ branched alcohol, preferably ethanol; the tetraalkyl orthosilicate is an orthosilicate of linear $C_1$-$C_4$ alcohol or branched $C_3$-$C_4$ alcohol, preferably tetraethyl orthosilicate (TEOS). The concentration of solute ammonia in the ammonia water is 1-25 wt %, preferably 20-25 wt %; and the ratio between the usage amounts of the alcohol, the solute ammonia in ammonia water and the tetraalkyl orthosilicate is 20-100 mL: 0.5-2.5 g: 1 g. The hydrolysis conditions are preferably as follows: reacting in the air at 0-50° C. for 1-10 h, and the drying conditions are as follows: drying in the air at 90-150° C. for 4-24 h.

In step c), the template agent is one or more of tetrapropylammonium hydroxide (TPAOH), tetrapropylammonium bromide (TPABr) and tetrapropylammonium chloride (TPACl), preferably TPAOH. In an embodiment, the TPAOH is used in a form of 25-40 wt % aqueous solution. The molar ratio of the silica gel loaded with metal nanoparticles to the template agent is 1:0.1-0.5, wherein the molar amount of the silica gel loaded with metal nanoparticles can be determined according to the molar amount of the tetraalkyl orthosilicate used in the step b). The conditions of the hydrothermal method are preferably as follows: reacting at 160-200° C. in a hydrothermal kettle for 3-5 days, and the conditions of calcination at a high temperature are as follows: calcining at 400 to 600° C. in air for 1-6 h.

In step d), the solvent is one or more of a $C_1$-$C_4$ linear alcohol, a $C_3$-$C_4$ branched alcohol, benzene and toluene, preferably ethanol and/or toluene. The organic-base silane coupling agents which can be used is as described above. The ratio between the usage amounts of the organic-base silane coupling agent, the silicalite-1 molecular sieve and the solvent is 0.01-5 mmol: 1 g: 20-100 mL. The reaction conditions are as follows: reacting at 30-100° C. for 4-24 h.

Preferably, in the above preparation methods, the amounts of the used soluble metal salt and the used organic-base silane coupling agent are theoretically capable of obtaining the catalyst with a content range of each component defined above.

Figure 1:
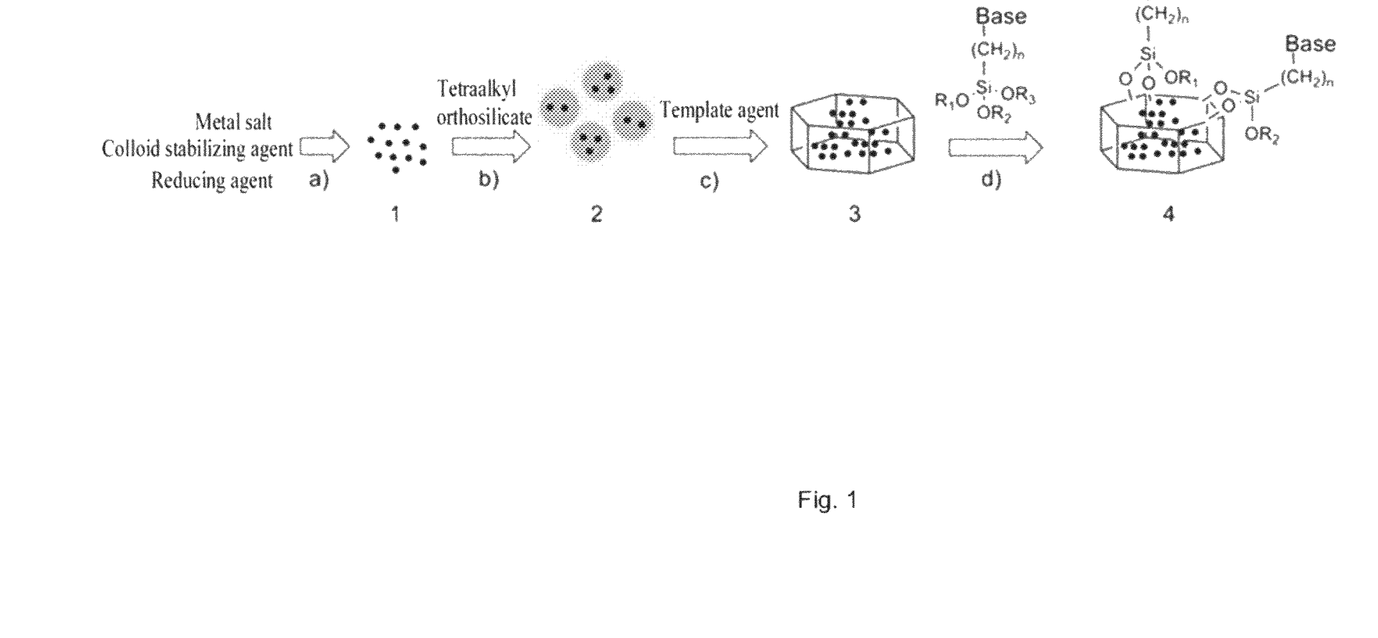
FIG. 1 is a schematic view showing the flow of the above-mentioned preparation method and the structures of intermediate products and final products of the catalyst.

FIG. 1 is a schematic view showing the flow of the above-mentioned preparation method and the structures of intermediate products and final products of the catalyst. It should be noted that any one, two or three of —$OR_1$, —$OR_2$, —$OR_3$ groups attached to Si in the molecule of the organic-base silane coupling agent can react with the silicon hydroxy groups on the surface of the silicalite-1 molecular sieve in the solvent, and any one, two or three of $R_1$, $R_2$, and $R_3$ are removed, whereby the organic basic groups of the organic-base silane coupling agent are attached to the surface of the silicalite-1 molecular sieve. Accordingly, a person skilled in the art will understand that the connection structure shown by reference sign 4 of FIG. 1 is merely illustrative and not limiting.

Another aspect of the present invention provides a method for preparing 1,2-pentanediol by hydrogenolysis of furfuryl alcohol using said catalyst, wherein when the reaction is carried out in a batch kettle, an aqueous solution of furfuryl alcohol with a mass percentage concentration of 20-100% (it is pure furfuryl alcohol when the mass percentage is 100%, the same applies hereinafter) is used, the usage amount of the catalyst is 0.1-10 wt %, preferably 0.5-5 wt % based on the mass of the solute furfuryl alcohol (calculated as solute); the reaction temperature is 50-200° C., preferably 60-120° C.; the hydrogen pressure (gauge pressure) is 0.5-10 MPa, preferably 1-5 MPa; the reaction time is 1-24 hours, preferably 2-6 hours.

when the reaction is carried out in a fixed bed reactor, an aqueous solution of furfuryl alcohol with a mass percentage concentration of 20-100% is used, the mass space velocity of furfuryl alcohol (calculated as solute)/catalyst is 0.5-4 $h^{-1}$, preferably 1-3 $h^{-1}$; the volume space velocity of hydrogen/catalyst is 500-1500 $h^{-1}$, preferably 800-1200 $h^{-1}$; the reaction temperature is 50-200° C., preferably 60-120° C.; and the hydrogen pressure (gauge pressure) is 0.5-10 MPa, preferably 1-5 MPa.

In the method for preparing 1,2-pentanediol, the catalyst is preferably in-situ reduced in hydrogen before use, and the reduction conditions are as follow: the gauge pressure of hydrogen is 0.1-1 MPa, preferably 0.2-0.4 MPa; the flow rate of $H_2$ per 100 g of catalyst is 0.5-20 L/min, preferably 1-15 L/min; the reduction temperature is 50-250° C., preferably 100-200° C.; the reduction time is 1-10 hours, preferably 2-6 hour.

Further, the present invention also provides the use of said catalyst for preparing 1,2-pentanediol by hydrogenolysis of furfuryl alcohol.

Compared with the prior art, the catalyst of the present invention has the following technical effects:

(1) The silicalite-1 molecular sieve has high thermal stability, and the metal nanoparticles are encapsulated therein to protect the metal nanoparticles from being covered by possible polymers, so that the catalyst has good stability;

(2) The silicalite-1 molecular sieve controls the diffusion of molecules in the pores by its regular pores, thereby exerting a good effect on shape selectivity. Therefore, the catalyst of the present invention significantly improves the selectivity of 1,2-pentanediol in the hydrogenolysis reaction of furfuryl alcohol;

(3) After the surface of the silicalite-1 molecular sieve is modified by an organic-base silane coupling agent, the raw material of furfuryl alcohol is in an alkaline environment before contacting the active metal, whereby the polymeric side reaction (resinification) of the furfuryl alcohol is inhibited. The furfuryl alcohol raw material is in a near-neutral state when it enters the pores and contacts the metal, and can react rapidly. Thereby the contradiction between the inhibition of the hydrogenolysis process of furfuryl alcohol in an alkaline environment (thereby reducing the 1,2-pentanediol selectivity) and the generation of more polymeric by-products from furfuryl alcohol in a neutral environment is solved effectively;

(4) Since the metal nanoparticles and the organic-base are immobilized on the silicalite-1 molecular sieve, when used in a batch reactor, the catalyst can be recovered and reused by simple filtration after completion of the reaction; or it can also be used for a fixed bed reaction, the reaction cost and the difficulty to separate the catalyst and the product are greatly reduced.

In the method for preparing 1,2-pentanediol by the hydrogenolysis of furfuryl alcohol using the catalyst of the present invention, the reaction conversion rate is more than 99%, the 1,2-pentanediol selectivity is up to 83.5%, and the catalytic performance of the catalyst can remain stable after reused for many times or a long-term use.

DESCRIPTION OF THE REFERENCE SIGNS

In FIG. 1,
1. The colloid of metal nanoparticles;
2. The silica gel loaded with metal nanoparticles;
3. The silicalite-1 molecular sieve encapsulated with metal nanoparticles;
4. The catalyst of the present invention.

EMBODIMENTS

The present invention will be further described in conjunction with embodiments, and it should be noted that the embodiments are not intended to limit the scope of the present invention.

The reagents in the present invention were mainly purchased from Sinopharm Chemical Reagent Co., Ltd., and the organic-base silane coupling agent was purchased from Sigma-Aldrich.

In the following examples and comparative examples, "%" used is "molar percentage" unless otherwise specified.

Transmission electron microscopy (TEM) was performed on an instrument of JEM-2100F (JEOL, Japan) using an accelerating voltage of 200 kV.

Infrared spectroscopy (FTIR) was performed on a Bruker Equinox 55 Fourier infrared spectrometer using a KBr pellet with a scan wavelength range of 4000-400 $cm^1$.

The structure of the pores was determined by $N_2$ isothermal adsorption and desorption (77K) using an instrument of Quantachrome Autosorb-1-CTCD-MS. The catalyst samples were degassed at 250° C. for 12 h before testing. The specific surface area ($S_{BET}$) was calculated from the relative pressure ($P/P_0$) data of 0.05-0.20. The pore volume ($V_p$) was the adsorption amount at the maximum relative pressure ($P/P_0$ 0.99). The pore diameter was calculated from the adsorption branch data through Barrett-Joyner-Halenda formula.

The test instrument used for estimating the performance of the catalyst is a Shimadzu GC-2010 gas chromatograph (hydrogen flame detector, with nitrogen as a carrier gas), which is equipped with a DB-5 capillary column (the fixed solution thereof is 5% of phenyl methyl siloxane, 30 m×0.32 mm×0.25 μm) and a hydrogen flame detector (FID). The temperature of the sample injector and detector were both 280° C.; the column temperature was programmed as follows: the column temperature was initially maintained at 100° C. for 0.5 minutes, and the temperature was raised to 260° C. at 15° C./min and maintained for 5 minutes. The column pressure was 8.5868 psi (approximately 59.2 kPa), the flow rate was 1.5 mL/min. Sample injection amount: 0.2 μL. The conversion rate and the selectivity were calculated using the area normalization method.

Examples 1-9

1. Catalyst Preparation

In Examples 1-9, Catalysts 1 #-9 # were prepared by using different soluble metal salts and organic-base silane coupling agents respectively, according to the following steps.

a) polyvinylpyrrolidone (PVP) was added to an aqueous solution containing a soluble metal salt (with a concentration of 1 mmol/L) and stirred at 0° C. for 30 min, and an aqueous solution of $NaBH_4$ (0.1 mol/L) was added rapidly, wherein the ratio between the usage amounts of PVP, the soluble metal salt and the aqueous solution of $NaBH_4$ was 11.2 g: 1 mmol: 100 mL, and stirred for 2 hours to obtain a colloid of metal nanoparticles;

b) under stirring, ethanol and 25 wt % of concentrated ammonia water were added to the above colloid of metal nanoparticles, and 346.67 g of tetraethyl orthosilicate (TEOS) was added, the ratio between the usage amounts of the ethanol, the concentrated ammonia water and TEOS was 50 mL: 5 mL: 1 g; after 8 h, the water and the ethanol were distilled off, and the residue was dried at 100° C. overnight to obtain a silica gel loaded with metal nanoparticles;

c) the silica gel loaded with metal nanoparticles obtained in step b) was uniformly mixed with a 40 wt % aqueous solution of TPAOH, and then transferred to a hydrothermal kettle, wherein the molar ratio of the silica gel loaded with metal nanoparticles to TPAOH was 1:0.3; the mixture obtained was treated at 180° C. for 3 days, filtered, dried at 100° C. overnight, and calcined at 550° C. for 4 h to obtain a silicalite-1 molecular sieve encapsulated with metal nanoparticles;

d) an organic-base silane coupling agent and the silicalite-1 molecular sieve encapsulated with metal nanoparticles obtained in step c) were added to ethanol, wherein the ratio between the amounts of the ethanol and the silicalite-1 molecular sieve encapsulated with metal nanoparticles was 50 ml: 1 g; and then the mixture obtained was reacted at 80° C. for 8 h, filtered, and dried at 100° C. overnight to obtain the Catalysts 1 #-9 # of the present invention.

Table 1 shows the types and contents of metal nanoparticles encapsulated by per 100 g of the silicalite-1 molecular sieve without surface-modification (i.e., pure $SiO_2$) in the catalysts prepared in Examples 1-9, the usage amounts of soluble metal salts in the step a) of Examples 1-9, and the types and usage amounts of the organic-base silane coupling agents used in step d), wherein the soluble metal salt used in each of the examples was the above-mentioned soluble metal salt corresponding to the metal shown in Table 1. The content of the encapsulated metal nanoparticles can be calculated according to the following formula: $(m_c - m_{SiO2})/m_{SiO2} \times 100\%$; wherein $m_c$ is the mass of the silicalite-1 molecular sieve encapsulated with metal nanoparticles obtained in step c), and $m_{SiO2}$ is the converted mass of pure $SiO_2$, which is calculated from the amount of alkyl orthosilicate used in step b).

TABLE 1

Preparation conditions for Catalyst 1#-9#

| Catalyst | Metal | Content of metal wt % | Usage amount of soluble metal salt mmol | Organic-base silane coupling agent | Usage amount of organic-base mmol |
|---|---|---|---|---|---|
| 1# | Ni | 4 | 68.14 | 3-aminopropyltriethoxysilane | 50 |
| 2# | Co | 4.5 | 76.40 | 3-(2-aminoethylamino)propyltrimethoxysilane | 100 |
| 3# | Cu | 5 | 78.74 | diethylenetriaminopropyltrimethoxysilane | 150 |
| 4# | Ru | 0.8 | 7.92 | 3-(dimethylamino)propyltriethoxysilane | 200 |
| 5# | Rh | 1.2 | 11.66 | diethylenetriaminopropyltrimethoxysilane | 250 |
| 6# | Pd | 1.0 | 9.40 | 3-(dimethylamino)propyltriethoxysilane | 300 |
| 7# | Ir | 1.8 | 9.37 | 3-aminopropyltriethoxysilane | 350 |
| 8# | Pt | 0.4 | 2.05 | 3-(2-aminoethylamino)propyltrimethoxysilane | 400 |
| 9# | Au | 1.6 | 8.12 | 3-(dimethylamino)propyltriethoxysilane | 450 |

Figure 2:
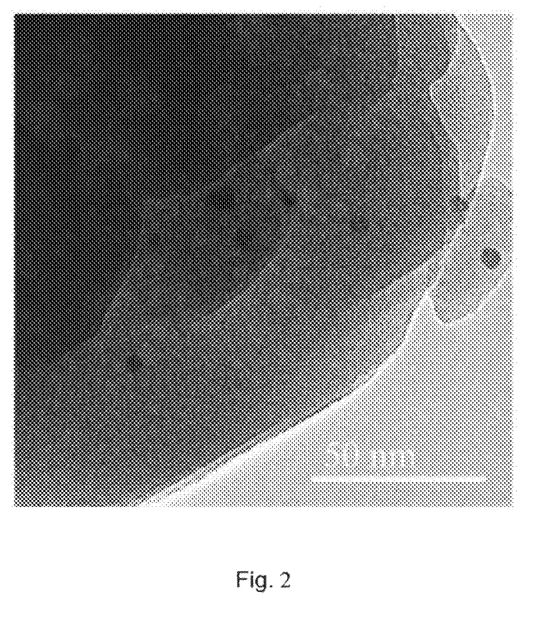
FIG. 2 is a TEM photograph of the Catalyst 1 # prepared in Example 1 of the present invention.

FIG. 2 is a transmission electron microscopy (TEM) photograph of Catalyst 1 # prepared in Example 1, and it can be seen that the metal nanoparticles (black dots in the photograph) are all at the inside of the silicalite-1 molecular sieve instead of the edge thereof, indicating that the metal nanoparticles are well encapsulated in the molecular sieve.

Figure 4:
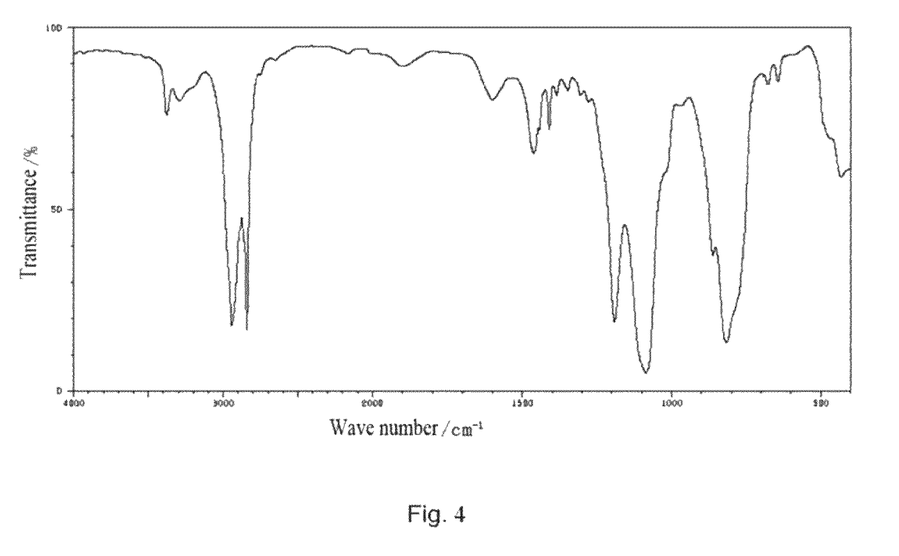
FIG. 4 is a FTIR spectrum of the Catalyst 1 # prepared in Example 1 of the present invention.

As shown in FIG. 4, in the apparent absorption peaks of the infrared spectrum (FTIR) diagram of Catalyst 1 #, the wavelengths of 3500, and 3400 cm$^{-1}$ are the characteristic absorptions of —NH$_2$, and the wavelengths of 2925, 2825 and 1470 cm$^{-1}$ are the characteristic absorptions of —CH2-, indicating that the organic-base has been grafted onto the silicalite-1 molecular sieve encapsulated with metal nanoparticles.

The silicalite-1 molecular sieve encapsulated with the nanoparticles of metal Ni and Catalyst 1 # were characterized by N$_2$ isothermal adsorption and desorption. The specific surface area, pore volume and pore diameter of the two were shown in Table 2 below.

TABLE 2

Characterization results of N$_2$ isothermal adsorption and desorption

| Sample | Specific surface area m$^2$/g | Pore volume cm$^3$/g | Pore diameter nm |
|---|---|---|---|
| Silicalite-1 molecular sieve encapsulated with the nanoparticles of metal Ni | 838 | 0.439 | 0.55 |
| Catalyst 1# | 837 | 0.438 | 0.55 |

It can be seen from the above results that there was no significant change on the pore structure of the silicalite-1 molecular sieve after grafted with organic-base, indicating that the organic-base was grafted on the outer surface of the silicalite-1 molecular sieve.

2. Evaluation of Catalyst Performance 2.1 Batch Kettle

Evaluations of the catalysts of the present invention were carried out in a batch kettle having a volume of 3000 mL and a material of stainless steel. A certain amount of catalyst was added to the batch kettle, and reduced in situ to activate the same. The mass percentages of the amount of added catalysts relative to the amount of furfuryl alcohol for hydrogenolysis (calculated as solute) are shown in Table 3. The reduction temperature was 200° C., the pressure of H$_2$ was 0.3 MPa, the flow rate of H$_2$ was 1.5 L/min, and the reduction was carried out for 4 hours.

After the above reduction, the temperature of the reaction kettle was lowered to the reaction temperature for hydrogenolysis of furfuryl alcohol, 2000 g of aqueous solution of furfuryl alcohol with a certain concentration was added, the temperature was again adjusted to the reaction temperature for hydrogenolysis, and hydrogen with a certain pressure was charged to start the reaction. After a certain period of reaction, the temperature was lowered and the pressure was released. A liquid sample was taken and analyzed by the above gas chromatography equipped with DB-5 capillary column and flame ion (FID) detector. The specific reaction conditions and the evaluation of catalyst performance are shown in Table 3.

The catalysts of the present invention were reused in the batch reaction kettle by the following method: after the reaction in the previous kettle was completed, the reaction liquid was removed through a filter placed inside the reactor, the catalyst was left in the reaction kettle; 2000 g of aqueous solution of furfuryl alcohol with a certain concentration was added again, the temperature was adjusted to the reaction temperature, and hydrogen with a certain pressure was charged to start the reaction, which ended after a certain period of time, the specific conditions were the same as those in the previous reaction.

TABLE 3

Reaction conditions and evaluation results of catalyst performance using catalysts 1#-9# of the present invention in the batch reaction kettle

| | Reaction conditions | | | | | Used for the first time | | Reused for 20 times | |
|---|---|---|---|---|---|---|---|---|---|
| Catalyst | Concentration of furfuryl alcohol wt % | Catalyst/furfuryl alcohol wt % | Reaction temperature ° C. | Hydrogen pressure MPa | Reaction time h | Conversion rate % | Selectivity % | Conversion rate % | Selectivity % |
| 1# | 50 | 9 | 100 | 3.5 | 2.5 | 99.2 | 65.0 | 99.5 | 65.3 |
| 2# | 60 | 7 | 95 | 4 | 3 | 99.7 | 64.3 | 99.6 | 64.2 |
| 3# | 40 | 8 | 100 | 5 | 4 | 99.5 | 71.8 | 99.7 | 71.9 |
| 4# | 90 | 4 | 105 | 3 | 3.5 | 99.3 | 76.0 | 99.2 | 76.4 |
| 5# | 70 | 3 | 120 | 2 | 4 | 99.4 | 67.3 | 99.5 | 67.1 |
| 6# | 80 | 2 | 90 | 1.5 | 5.6 | 99.3 | 76.9 | 99.3 | 76.8 |
| 7# | 30 | 5 | 110 | 2.5 | 4.8 | 99.2 | 77.5 | 99.2 | 77.4 |
| 8# | 20 | 2.5 | 85 | 1 | 3.2 | 99.7 | 83.4 | 99.8 | 83.5 |
| 9# | 100 | 1 | 115 | 4.5 | 6 | 99.9 | 80.2 | 99.5 | 80.1 |

As can be seen from Table 3, catalysts 1 #-9 # prepared in Examples 1-9 of the present invention showed good activity and 1,2-pentanediol selectivity for the hydrogenolysis of furfuryl alcohol. High conversion rates were obtained at relatively low reaction temperatures. In particular, the catalysts of the present invention have excellent stabilities, and the activities thereof can be substantially maintained after 20 times of reuse.

2.2 Fixed Bed

Evaluation of the catalyst of the present invention were carried out in a fixed bed reactor, which is a stainless steel tube having an outer diameter of 40 mm, an inner diameter of 20 mm and a length of 1000 mm. 50 g of the catalyst was charged into the reactor, and the catalyst was reduced in situ before the reaction, the reduction temperature was 200° C., the pressure of $H_2$ was 0.3 MPa, the flow rate of $H_2$ was 1.5 L/min, and the reduction was carried out for 4 hours. After the reduction ended, the temperature was lowered to the reaction temperature, the hydrogen/catalyst volume space velocity was set to 1000 $h^{-1}$, the flow rate of the aqueous solution of furfuryl alcohol was adjusted to obtain the desired furfuryl alcohol (calculated as solute)/catalyst mass space velocity, and the pressure was adjusted to the required reaction pressure. The specific reaction conditions are shown in Table 4. A liquid sample was taken online and analyzed by the gas chromatography with DB-5 capillary column and flame ion (FID) detector as described above.

TABLE 4

Reaction conditions and evaluation results of catalyst performance of the reaction using catalysts 1#-9# of the present invention in the fixed bed reactor

| | Reaction conditions | | | | After running for 10 h | | After running for 500 h | |
|---|---|---|---|---|---|---|---|---|
| Catalyst | Concentration of furfuryl alcohol wt % | Temperature ° C. | Hydrogen pressure MPa | Furfuryl alcohol/ catalyst mass space velocity $h^{-1}$ | Conversion rate % | Selectivity % | Conversion rate % | Selectivity % |
| 1# | 50 | 100 | 5.5 | 2.5 | 99.2 | 65.0 | 99.3 | 64.9 |
| 2# | 60 | 95 | 6 | 3 | 99.7 | 64.3 | 99.6 | 64.5 |
| 3# | 40 | 100 | 4.5 | 2 | 99.5 | 71.8 | 99.5 | 72.0 |
| 4# | 90 | 105 | 8 | 1.5 | 99.3 | 76.0 | 99.4 | 75.8 |
| 5# | 70 | 120 | 7 | 1 | 99.4 | 67.3 | 99.2 | 67.7 |
| 6# | 80 | 90 | 9 | 1.6 | 99.3 | 76.9 | 99.5 | 77.0 |
| 7# | 30 | 110 | 10 | 1.8 | 99.2 | 77.5 | 99.3 | 77.8 |
| 8# | 20 | 85 | 7.5 | 2 | 99.7 | 83.4 | 99.8 | 83.5 |
| 9# | 100 | 115 | 8.5 | 2.2 | 99.9 | 80.2 | 99.8 | 80.1 |

As can be seen from Table 4, in the fixed bed reactor, catalysts 1 #-9 # showed good activity and 1,2-pentanediol selectivity for the hydrogenolysis of furfuryl alcohol, and the life test of 500 h showed that the catalysts of the present invention had excellent stabilities.

Comparative Examples 1-9

As to Comparative Examples 1-9, the catalysts in which the metal nanoparticles were loaded on the outer surface of the organic-base-functionalized silicalite-1 molecular sieve were prepared as Comparative Catalysts 1-1 #-1-9 #, respectively.

a) ethanol and 25 wt % of concentrated ammonia water were mixed under stirring, 346.67 g of tetraethyl orthosilicate (TEOS) was added, and the ratio between the usage amounts of ethanol, concentrated ammonia and TEOS was 50 mL: 5 mL: 1 g; after 8 h, the water and ethanol was distilled off, and the residue was dried at 100° C. overnight to obtain 100 g of silica gel;

b) the silica gel obtained in step a) was uniformly mixed with 40 wt % of aqueous solution of TPAOH and transferred to a hydrothermal kettle, wherein the molar ratio of silica gel to TPAOH was 1:0.3; and then the silica gel was treated at 180° C. for 3 days, filtered, dried at 100° C. overnight, and calcinated at 550° C. for 4 h to obtain a silicalite-1 molecular sieve;

c) an organic-base silane coupling agent and the silicalite-1 molecular sieve obtained in the step b) were added to ethanol, wherein the ratio of the amount of ethanol to the silicalite-1 molecular sieve was 50 ml: 1 g; the organic-base silane coupling agent and the silicalite-1 molecular sieve were reacted at 80° C. for 8 h, filtered, and dried at 100° C. overnight to obtain an organic-base functionalized silicalite-1 molecular sieve;

d) polyvinylpyrrolidone (PVP) was added to an aqueous solution containing a soluble metal salt (with a concentration of 1 mmol/L), and stirred at 0° C. for 30 min, and then an aqueous solution of $NaBH_4$ (0.1 mol/L) was rapidly added, wherein the ratio between the usage amounts of PVP, the soluble metal salt and the aqueous solution of $NaBH_4$ was 11.2 g: 1 mmol: 100 mL, and stirred for 2 h to obtain a colloid of metal nanoparticles;

e) the organic-base functionalized silicalite-1 molecular sieve obtained in the step c) was added to the colloid of metal nanoparticles obtained in the step d), stirred for 8 hours, filtered, and dried at 100° C. overnight to obtain Comparative Catalysts 1-1 #-1-9 #.

Table 5 shows the types and contents of metal nanoparticles loaded on per 100 g of the silicalite-1 molecular sieve without surface-modification (i.e., pure $SiO_2$) in the catalysts prepared in Comparative Examples 1-9, the usage amounts of soluble metal salts in step a) of Comparative Examples 1-9, and the types and amounts of the organic-base silane coupling agents used in the step c), wherein the soluble metal salt used in each of the Comparative Examples was the above-mentioned soluble metal salt corresponding to the metal shown in Table 5.

TABLE 5

Preparation conditions for Comparative Catalysts 1-1#-1-9#

| Catalyst | Metal | Content of metal wt % | Usage amount of soluble metal salt mmol | Organic-base silane coupling agent | Usage amount of organic-base mmol |
|---|---|---|---|---|---|
| 1-1# | Ni | 4 | 68.14 | 3-aminopropyltriethoxysilane | 50 |
| 1-2# | Co | 4.5 | 76.40 | 3-(2-aminoethylamino)propyltrimethoxysilane | 100 |
| 1-3# | Cu | 5 | 78.74 | diethylenetriaminopropyltrimethoxysilane | 150 |
| 1-4# | Ru | 0.8 | 7.92 | 3-(dimethylamino)propyltriethoxysilane | 200 |
| 1-5# | Rh | 1.2 | 11.66 | diethylenetriaminopropyltrimethoxysilane | 250 |
| 1-6# | Pd | 1.0 | 9.40 | 3-(dimethylamino)propyltriethoxysilane | 300 |
| 1-7# | Ir | 1.8 | 9.37 | 3-aminopropyltriethoxysilane | 350 |
| 1-8# | Pt | 0.4 | 2.05 | 3-(2-aminoethylamino)propyltrimethoxysilane | 400 |
| 1-9# | Au | 1.6 | 8.12 | 3-(dimethylamino)propyltriethoxysilane | 450 |

Figure 3:
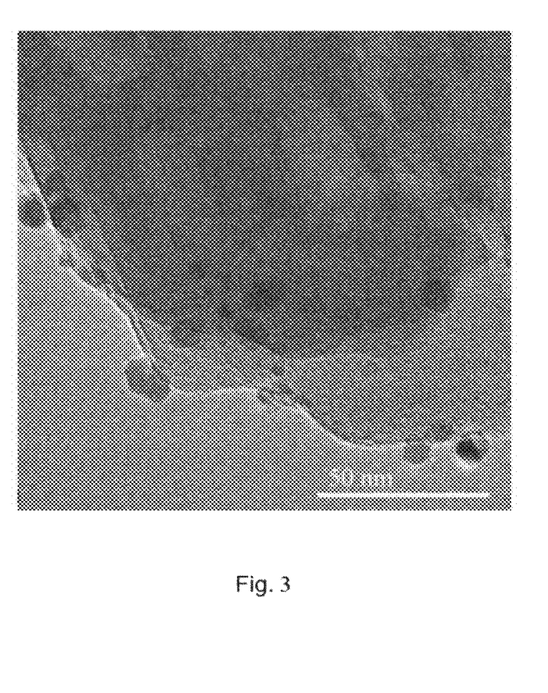
FIG. 3 is a TEM photograph of the Catalyst 1-1 # prepared in Comparative Example 1.

FIG. 3 is a transmission electron microscopy (TEM) photograph of the Catalyst 1-1 #. It can be seen that the metal nanoparticles (black dots in the graph) are at the edge of the silicalite-1 molecular sieve, indicating that the metal nanoparticles are on the outer surface of the molecular sieve.

After activated, Comparative Catalysts 1-1 #-1-9 # were used for the reaction of hydrogenolysis of furfuryl alcohol to prepare 1,2-pentanediol, and the performance evaluation and reuse were carried out in the same manner as in Examples 1-9. The results of the performance evaluation are shown in Table 6 below.

protection of the silical-1 molecular sieve, it is inevitable that some of the active sites of the metal nanoparticles are covered, the stability is not good, and the activity decreased significantly only after 5 times of reuse.

Comparative Examples 10-18

As to Comparative Examples 10-18, the same preparation methods as in Examples 1-9 were carried out without implementing step d), and the catalysts in which metal nanoparticles were encapsulated in a silicalite-1 molecular

TABLE 6

Performance evaluation results of Comparative Catalysts 1-1#-1-9#

| | Reaction conditions | | | | | Used for the first time | | Reused for 5 times | |
|---|---|---|---|---|---|---|---|---|---|
| Catalyst | Concentration of furfuryl alcohol wt % | Catalyst/furfuryl alcohol wt % | Reaction temperature ° C. | Hydrogen pressure MPa | Reaction time h | Conversion rate % | Selectivity % | Conversion rate % | Selectivity % |
| 1-1# | 50 | 9 | 100 | 3.5 | 2.5 | 92.7 | 15.0 | 59.3 | 15.1 |
| 1-2# | 60 | 7 | 95 | 4 | 3 | 89.3 | 14.3 | 44.0 | 14.2 |
| 1-3# | 40 | 8 | 100 | 2.5 | 4 | 83.5 | 21.8 | 38.6 | 21.4 |
| 1-4# | 90 | 4 | 105 | 3 | 3.5 | 94.1 | 26.0 | 62.4 | 25.8 |
| 1-5# | 70 | 3 | 120 | 2 | 4 | 85.9 | 17.3 | 57.2 | 17.4 |
| 1-6# | 80 | 2 | 90 | 1.5 | 5.6 | 76.4 | 16.9 | 37.1 | 16.8 |
| 1-7# | 30 | 5 | 110 | 2 | 4.8 | 75.6 | 19.5 | 40.5 | 19.9 |
| 1-8# | 20 | 2.5 | 85 | 3.5 | 3.2 | 83.8 | 33.4 | 46.7 | 32.7 |
| 1-9# | 100 | 1 | 115 | 4.5 | 6 | 89.0 | 20.2 | 58.4 | 19.9 |

As can be seen from Table 6, since the metal nanoparticles are on the outer surface of the organic-base functionalized silicalite-1 molecular sieve, the furfuryl alcohol molecules and the metal nanoparticles are both in an alkaline environment, the shape selectivity of the pores of the silicalite-1 molecular sieve cannot be utilized, therefore, the activity and the 1,2-pentanediol selectivity of Catalysts 1-1 #-1-9 # for the hydrogenolysis of furfuryl alcohol are significantly lower than that of Catalysts 1 #-9 #; in addition, although the polymerization of furfuryl alcohol was obviously reduced during the reaction, but due to lack of the encapsulation sieve without organic-base functionalization were prepared as Comparative Catalysts 2-1 #-2-9 #.

The Comparative Catalysts 2-1 #-2-9 # were activated in the batch kettle, and the activation conditions were the same as those in Examples 1-9. Subsequently, the reaction for preparing 1,2-pentanediol by hydrogenolysis of furfuryl alcohol was carried out using Comparative Catalysts 2-1 #-2-9 #, and the performance evaluations of Comparative Catalysts 2-1 #-2-9 # were carried out in the same manner as in Examples 1-9. The results are shown in Table 7 below.

TABLE 7

Performance evaluation results of Comparative Catalyst 2-1#-2-9#

| | Reaction conditions | | | | | Used for the first time | | Reused for 5 times | |
|---|---|---|---|---|---|---|---|---|---|
| | Concentration | | | | | | | | |
| Catalyst | of furfuryl alcohol wt % | Catalyst/furfuryl alcohol wt % | Reaction temperature °C. | Hydrogen pressure MPa | Reaction time h | Conversion rate % | Selectivity % | Conversion rate % | Selectivity % |
| 2-1# | 50  | 9   | 100 | 3.5 | 2.5 | 92.2 | 13.0 | 81.2 | 12.2 |
| 2-2# | 60  | 7   | 95  | 4   | 3   | 90.7 | 22.1 | 80.7 | 20.0 |
| 2-3# | 40  | 8   | 100 | 2.5 | 4   | 91.5 | 20.6 | 75.5 | 17.1 |
| 2-4# | 90  | 4   | 105 | 3   | 3.5 | 92.3 | 23.4 | 84.3 | 18.7 |
| 2-5# | 70  | 3   | 120 | 2   | 4   | 98.4 | 18.5 | 72.4 | 14.6 |
| 2-6# | 80  | 2   | 90  | 1.5 | 5.6 | 93.3 | 20.9 | 85.3 | 16.3 |
| 2-7# | 30  | 5   | 110 | 2   | 4.8 | 95.2 | 23.2 | 81.2 | 19.9 |
| 2-8# | 20  | 2.5 | 85  | 3.5 | 3.2 | 91.7 | 31.7 | 76.7 | 25.4 |
| 2-9# | 100 | 1   | 115 | 4.5 | 6   | 98.9 | 21.5 | 82.9 | 17.8 |

As can be seen from Table 7, since no organic-base is present on the outer surface of the silicalite-1 molecular sieve, the furfuryl alcohol molecules undergo obvious polymerization after being heated, and thus the conversion rate is at a higher level. However, although the metal nanoparticles are encapsulated in the silicalite-1 molecular sieve, the amount of furfuryl alcohol which can reach the metal nanoparticles is reduced due to the side reaction of polymerization, and finally the selectivity of 1,2-pentanediol is low. Furthermore, the polymerization of more furfuryl alcohol also brings the problem of poor catalyst stability, and the activity of the catalyst decreases to some extend after 5 times of reuse.

As can be seen, in order to ensure high activity, high 1,2-pentanediol selectivity and good stability of the catalyst, both the encapsulation of the metal nanoparticles in the molecular sieve and the functionalization of the organic-base on the outer surface are indispensable.

The contents described above are only preferred embodiments of the present invention, but the scope of the present invention is not limited thereto, and any changes or substitutions that may be readily conceived by those skilled in the art are intended to be included within the scope of the present invention.

The invention claimed is:

1. A catalyst for preparing 1,2-pentanediol by hydrogenolysis of furfuryl alcohol, wherein the catalyst comprises a carrier and an active component, the carrier is a silicalite-1 molecular sieve surface-modified with an organic-base silane coupling agent, the active component is metal nanoparticles encapsulated in the pores of the silicalite-1 molecular sieve,
wherein the organic-base silane coupling agent is a compound represented by the following general formula (1):

wherein, -Base in the general formula (1) represents an organic basic group; $R_1$, $R_2$ and $R_3$ represent $C_1$-$C_4$ alkyls, which are the same or different from each other; n is 1-10;

wherein the metal nanoparticle is one or more of Ni, Co, Cu, Ru, Rh, Pd, Ir, Pt and Au.

2. The catalyst according to claim 1, wherein
the organic-base silane coupling agent is one or more of 3-aminopropyltriethoxysilane, 3-(2-aminoethylamino)propyltrimethoxysilane, diethylenetriaminopropyltrimethoxysilane and 3-(dimethylamino)propyltriethoxysilane.

3. The catalyst according to claim 1, wherein the loading amount of the metal nanoparticle is 0.01-5 wt %, based on the mass of the silicalite-1 molecular sieve without surface-modification in the catalyst.

4. The catalyst according to claim 3, wherein the amount of the organic-base silane coupling agent is 0.01-5 mmol/g, based on the mass of the silicalite-1 molecular sieve without surface-modification in the catalyst.

5. A method for preparing the catalyst according to claim 1, wherein the method comprises the steps of:
a) reducing an aqueous solution of soluble metal salt by using a reducing agent in the presence of a colloid stabilizing agent to obtain a colloid of metal nanoparticles;
b) adding an alcohol, ammonia water and a tetraalkyl orthosilicate to the colloid of metal nanoparticles obtained in step a), and distilling to remove water and alcohol after hydrolyzation, and then drying to obtain a silica gel loaded with the metal nanoparticles;
c) crystallizing the silica gel loaded with the metal nanoparticles obtained in step b) by using hydrothermal method under the effect of a template agent, and calcinating at a high temperature to obtain a silicalite-1 molecular sieve encapsulated with metal nanoparticles;
d) modifying the surface of the silicalite-1 molecular sieve encapsulated with metal nanoparticles obtained in step c) by using an organic-base silane coupling agent in a solvent to obtain the catalyst.

6. The method according to claim 5, wherein in step a),
the soluble metal salt is one or more of a metal nitrate, a metal acetate and a metal chloride;
the colloid stabilizing agent is one or more of polyvinylpyrrolidone, polyethylene glycol, polyvinyl alcohol, Tween 20, Tween 80 and Span 20;
the reducing agent is one or more of $NaBH_4$, formaldehyde and hydrazine hydrate.

7. The method according to claim 5, wherein in step a), the concentration of the aqueous solution of soluble metal salt is 0.1-2 mmol/L, and the ratio between the usage amounts of the colloid stabilizing agent, the soluble metal salt and the reducing agent is 5-20 g:1 mmol:5-15 mmol.

8. The method according to claim 5, wherein in step b), the alcohol is a $C_1$-$C_4$ linear alcohol or a $C_3$-$C_4$ branched alcohol; the tetraalkyl orthosilicate is a orthosilicate of $C_1$-$C_4$ linear alcohol or $C_3$-$C_4$ branched alcohol; the concentration of solute ammonia in the ammonia water is 1-25 wt %; and the ratio between the usage amounts of the alcohol, the solute ammonia in ammonia water and the tetraalkyl orthosilicate is 20-100 mL:0.5-2.5 g:1 g.

9. The method according to claim 5, wherein in step c), the template agent is one or more of tetrapropylammonium hydroxide, tetrapropylammonium bromide and tetrapropylammonium chloride; the molar ratio of the silica gel loaded with the metal nanoparticles to the template agent is 1:0.1-0.5.

10. The method according to claim 5, wherein in step d), the solvent is one or more of a $C_1$-$C_4$ linear alcohol, a $C_3$-$C_4$ branched alcohol, benzene and toluene; the ratio between the usage amounts of the organic-base silane coupling agent, the silicalite-1 molecular sieve and the solvent is 0.01-5 mmol:1 g:20-100 mL, and the reaction conditions are as follows: reacting at 30-100° C. for 4-24 h.

11. A method for preparing 1,2-pentanediol by hydrogenolysis of furfuryl alcohol using the catalyst according to claim 1, comprising:
   reacting, in a batch kettle, an aqueous solution of furfuryl alcohol with a mass percentage concentration of 20-100% with hydrogen in the presence of the catalyst with an amount of 0.1-10 wt % based on the mass of the solute furfuryl alcohol; wherein the reaction temperature is 50-200° C.; the gauge pressure of hydrogen is 0.5-10 MPa; the reaction time is 1-24 hours; and
   or
   reacting, in a fixed bed reactor, an aqueous solution of furfuryl alcohol with a mass percentage concentration of 20-100% with hydrogen in the presence of the catalyst, wherein, the mass space velocity of the solute furfuryl alcohol/catalyst is 0.5-4 $h^{-1}$; the volume space velocity of hydrogen/catalyst is 500-1500 $h^{-1}$; the reaction temperature is 50-200° C.; and the gauge pressure of hydrogen is 0.5-10 MPa.

12. The method according to claim 11, wherein the catalyst needs to be in-situ reduced in hydrogen before use, and the reduction conditions are as follow: the gauge pressure of hydrogen is 0.1-1 MPa; the flow rate of $H_2$ per 100 g of used catalyst is 0.5-20 L/min; the reduction temperature is 50-250° C.; the reduction time is 1-10 hours.

13. The catalyst according to claim 2, wherein the loading amount of the metal nanoparticle is 0.01-5 wt %, based on the mass of the silicalite-1 molecular sieve without surface-modification in the catalyst.

14. The catalyst according to claim 2, wherein the loading amount of the metal nanoparticle is 0.1-2 wt %, the amount of the organic-base silane coupling agent is 0.1-2 mmol/g, based on the mass of the silicalite-1 molecular sieve without surface-modification in the catalyst.

15. The catalyst according to claim 1, wherein the loading amount of the metal nanoparticle is 0.1-2 wt %, the amount of the organic-base silane coupling agent is 0.1-2 mmol/g, based on the mass of the silicalite-1 molecular sieve without surface-modification in the catalyst.

16. The method according to claim 6, wherein in step a), the concentration of the aqueous solution of soluble metal salt is 0.1-2 mmol/L, and the ratio between the usage amounts of the colloid stabilizing agent, the soluble metal salt and the reducing agent is 5-20 g:1 mmol:5-15 mmol.

17. The method according to claim 6, wherein in step b), the alcohol is a $C_1$-$C_4$ linear alcohol or a $C_3$-$C_4$ branched alcohol; the tetraalkyl orthosilicate is a orthosilicate of $C_1$-$C_4$ linear alcohol or $C_3$-$C_4$ branched alcohol; the concentration of solute ammonia in the ammonia water is 1-25 wt %; and the ratio between the usage amounts of the alcohol, the solute ammonia in ammonia water and the tetraalkyl orthosilicate is 20-100 mL:0.5-2.5 g:1 g.

18. The method according to claim 6, wherein in step c), the template agent is one or more of tetrapropylammonium hydroxide, tetrapropylammonium bromide and tetrapropylammonium chloride; the molar ratio of the silica gel loaded with the metal nanoparticles to the template agent is 1:0.1-0.5.

19. The method according to claim 6, wherein in step d), the solvent is one or more of a $C_1$-$C_4$ linear alcohol, a $C_3$-$C_4$ branched alcohol, benzene and toluene; the ratio between the usage amounts of the organic-base silane coupling agent, the silicalite-1 molecular sieve and the solvent is 0.01-5 mmol:1 g:20-100 mL, and the reaction conditions are as follows: reacting at 30-100° C. for 4-24 h.

20. The method according to claim 6, wherein in step a),
   the soluble metal salt is chloroplatinic acid and/or chloroauric acid;
   the colloid stabilizing agent is polyvinylpyrrolidone;
   the reducing agent is $NaBH_4$;
   wherein in step b), the alcohol is ethanol; the tetraalkyl orthosilicate is tetraethyl orthosilicate (TEOS); the concentration of solute ammonia in the ammonia water is 20-25 wt %; and the ratio between the usage amounts of the alcohol, the solute ammonia in ammonia water and the tetraalkyl orthosilicate is 20-100 mL:0.5-2.5 g:1 g;
   wherein in step c), the template agent is tetrapropylammonium hydroxide in a form of 25-40 wt % aqueous solution; the molar ratio of the silica gel loaded with the metal nanoparticles to the template agent is 1:0.1-0.5;
   wherein in step d), the solvent is ethanol and/or toluene; the ratio between the usage amounts of the organic-base silane coupling agent, the silicalite-1 molecular sieve and the solvent is 0.01-5 mmol:1 g:20-100 mL, and the reaction conditions are as follows: reacting at 30-100° C. for 4-24 h.

21. The catalyst according to claim 1, wherein Base in the general formula (1) represents an amino or a polyamine group.

* * * * *